(12) United States Patent
Dewey et al.

(10) Patent No.: US 8,425,611 B2
(45) Date of Patent: Apr. 23, 2013

(54) EXPANDABLE ORTHOPEDIC IMPLANT SYSTEM AND METHOD

(75) Inventors: Jonathan Dewey, Raleigh, NC (US); Marco Dagoberto Capote, Boulder, CO (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 109 days.

(21) Appl. No.: 12/912,553

(22) Filed: Oct. 26, 2010

(65) Prior Publication Data
US 2012/0101576 A1    Apr. 26, 2012

(51) Int. Cl.
*A61F 2/44*    (2006.01)

(52) U.S. Cl.
USPC .................................. 623/17.16; 623/17.12

(58) Field of Classification Search ............... 623/17.11, 623/17.12, 17.15, 17.16
See application file for complete search history.

(56) References Cited

U.S. PATENT DOCUMENTS

| | | |
|---|---|---|
| 5,236,460 A | 8/1993 | Barber |
| 5,306,275 A | 4/1994 | Bryan |
| 5,733,284 A | 3/1998 | Martin |
| 5,776,198 A | 7/1998 | Rabbe et al. |
| 5,814,070 A | 9/1998 | Borzone et al. |
| 5,972,031 A | 10/1999 | Biedermann et al. |
| 5,989,256 A | 11/1999 | Kuslich et al. |
| 6,132,464 A | 10/2000 | Martin |
| 6,168,598 B1 | 1/2001 | Martello |
| 6,193,756 B1 | 2/2001 | Studer et al. |
| 6,200,348 B1 | 3/2001 | Biedermann et al. |
| 6,419,705 B1 | 7/2002 | Erickson |
| 6,547,795 B2 | 4/2003 | Schneiderman |
| 6,610,080 B2 | 8/2003 | Morgan |
| 6,610,091 B1 | 8/2003 | Reiley |
| 6,616,695 B1 | 9/2003 | Crozet et al. |
| 6,719,795 B1 | 4/2004 | Cornwall et al. |
| 6,773,436 B2 | 8/2004 | Donnelly et al. |
| 6,843,799 B2 | 1/2005 | Bartlett |
| 6,860,884 B2 | 3/2005 | Shirado et al. |
| 6,866,682 B1 | 3/2005 | An et al. |
| 6,974,478 B2 | 12/2005 | Reiley et al. |
| 7,041,136 B2 | 5/2006 | Goble et al. |
| 7,074,237 B2 | 7/2006 | Goble et al. |
| 7,074,238 B2 | 7/2006 | Stinson et al. |
| 7,087,082 B2 | 8/2006 | Paul et al. |
| 7,090,698 B2 | 8/2006 | Goble et al. |
| 7,163,540 B2 | 1/2007 | Martello |
| 7,544,208 B1 | 6/2009 | Mueller et al. |

(Continued)

FOREIGN PATENT DOCUMENTS

| | | |
|---|---|---|
| EP | 1 800 627 | 6/2007 |
| GB | 2198043 | 6/1988 |

(Continued)

*Primary Examiner* — Ellen C Hammond
*Assistant Examiner* — Atiya Mahmud

(57) ABSTRACT

An orthopedic implant includes a first member that defines a longitudinal axis, a first wall and a second wall. The first wall defines at least a portion of a chamber. The second wall defines a first graft containment cavity. The chamber is separate from the first graft containment cavity. A second member defines a first wall disposed for sealed engagement with the first wall of the first member. The first wall of the second member defines at least a portion of the chamber. The second member is configured for movement along the longitudinal axis relative to the first member. Methods of use are disclosed.

17 Claims, 8 Drawing Sheets

U.S. PATENT DOCUMENTS

| | | |
|---|---|---|
| 7,615,078 B2 | 11/2009 | White et al. |
| 7,648,529 B2 | 1/2010 | An et al. |
| 7,731,752 B2 | 6/2010 | Edie et al. |
| 7,803,191 B2 | 9/2010 | Biedermann et al. |
| 2002/0147497 A1 | 10/2002 | Belef et al. |
| 2003/0040746 A1 | 2/2003 | Mitchell et al. |
| 2004/0181283 A1 | 9/2004 | Boyer, II et al. |
| 2005/0033434 A1 | 2/2005 | Berry |
| 2005/0049705 A1 | 3/2005 | Hale et al. |
| 2005/0058790 A1 | 3/2005 | Simon et al. |
| 2005/0143825 A1 | 6/2005 | Enayati |
| 2006/0004457 A1* | 1/2006 | Collins et al. ............... 623/17.16 |
| 2006/0036324 A1 | 2/2006 | Sachs et al. |
| 2006/0058790 A1 | 3/2006 | Carl et al. |
| 2006/0058877 A1 | 3/2006 | Gutlin et al. |
| 2006/0058879 A1 | 3/2006 | Metz-Stavenhagen |
| 2006/0089646 A1 | 4/2006 | Bonutti |
| 2006/0100710 A1 | 5/2006 | Gutlin et al. |
| 2006/0149375 A1 | 7/2006 | Yuan et al. |
| 2006/0282076 A1 | 12/2006 | Labrom et al. |
| 2006/0287725 A1 | 12/2006 | Miller |
| 2006/0293663 A1 | 12/2006 | Walkenhorst et al. |
| 2007/0016191 A1 | 1/2007 | Culbert et al. |
| 2007/0055236 A1 | 3/2007 | Hudgins et al. |
| 2007/0088358 A1 | 4/2007 | Yuan et al. |
| 2007/0123868 A1 | 5/2007 | Culbert et al. |
| 2007/0162000 A1 | 7/2007 | Perkins |
| 2007/0173818 A1 | 7/2007 | Hestad et al. |
| 2007/0185492 A1 | 8/2007 | Chervitz et al. |
| 2007/0191834 A1 | 8/2007 | Bruneau et al. |
| 2007/0198091 A1 | 8/2007 | Boyer et al. |
| 2007/0233077 A1 | 10/2007 | Khalili |
| 2007/0233189 A1 | 10/2007 | Pedlick et al. |
| 2007/0233254 A1 | 10/2007 | Grotz et al. |
| 2007/0255411 A1 | 11/2007 | Reiley |
| 2007/0255413 A1 | 11/2007 | Edie et al. |
| 2007/0270964 A1* | 11/2007 | Strohkirch et al. ......... 623/17.11 |
| 2008/0058930 A1* | 3/2008 | Edie et al. .................. 623/17.11 |
| 2008/0114467 A1 | 5/2008 | Capote et al. |
| 2008/0116767 A1 | 5/2008 | Yu et al. |
| 2008/0147194 A1 | 6/2008 | Grotz et al. |
| 2008/0161926 A1 | 7/2008 | Melkent et al. |
| 2008/0161933 A1 | 7/2008 | Grotz et al. |
| 2008/0281424 A1 | 11/2008 | Parry et al. |
| 2008/0288073 A1* | 11/2008 | Renganath et al. ......... 623/17.12 |
| 2009/0105761 A1 | 4/2009 | Robie et al. |
| 2009/0138086 A1 | 5/2009 | Dewey |
| 2009/0138089 A1 | 5/2009 | Doubler et al. |
| 2009/0187248 A1 | 7/2009 | Dewey et al. |
| 2009/0270987 A1 | 10/2009 | Heinz |
| 2010/0057204 A1 | 3/2010 | Kadaba et al. |
| 2010/0114319 A1 | 5/2010 | Edie |
| 2010/0179657 A1 | 7/2010 | Greenhalgh et al. |
| 2010/0179658 A1* | 7/2010 | Freeman et al. ........... 623/17.12 |
| 2010/0198352 A1 | 8/2010 | Edie et al. |
| 2010/0204794 A1 | 8/2010 | Farzem et al. |
| 2010/0268338 A1 | 10/2010 | Melkent |

FOREIGN PATENT DOCUMENTS

| | | |
|---|---|---|
| WO | 9004948 | 5/1990 |
| WO | 2005037150 | 4/2005 |
| WO | 2005112835 | 12/2005 |
| WO | 2008086276 | 7/2008 |

* cited by examiner

EXPANDABLE ORTHOPEDIC IMPLANT SYSTEM AND METHOD

TECHNICAL FIELD

The present disclosure generally relates to medical devices for the treatment of bone disorders, and more particularly to an orthopedic implant system and method, which include members disposed in a telescopic arrangement that are expanded under fluid pressure to engage adjacent bone surfaces.

BACKGROUND

Spinal disorders such as degenerative disc disease, disc herniation, osteoporosis, spondylolisthesis, stenosis, scoliosis and other curvature abnormalities, kyphosis, tumor, and fracture may result from factors including trauma, disease and degenerative conditions caused by injury and aging. Spinal disorders typically result in symptoms including pain, nerve damage, and partial or complete loss of mobility.

Non-surgical treatments, such as medication, rehabilitation and exercise can be effective, however, may fail to relieve the symptoms associated with these disorders. Surgical treatment of these spinal disorders includes fusion, fixation, corpectomy, discectomy, laminectomy and implantable prosthetics. In procedures such as corpectomy and/or discectomy, fusion and fixation treatments may be performed that employ implants such as interbody fusion devices to restore the mechanical support function of the vertebrae. This disclosure describes an improvement over these prior art technologies.

SUMMARY OF THE INVENTION

Accordingly, an orthopedic implant system and related methods are provided for treating bone disorders. It is contemplated that the orthopedic implant system and methods include members disposed in a telescopic arrangement that are expandable under fluid pressure to engage adjacent bone surfaces. It is further contemplated that the orthopedic implant system is expanded hydraulically allowing for axial expansion.

In one particular embodiment, in accordance with the principles of the present disclosure, an orthopedic implant is provided. The orthopedic implant includes a first member that defines a longitudinal axis, a first wall and a second wall. The first wall defines at least a portion of a chamber. The second wall defines a first graft containment cavity. The chamber is separate from the first graft containment cavity. A second member defines a first wall disposed for sealed engagement with the first wall of the first member. The first wall of the second member defines at least a portion of the chamber. The second member is configured for movement along the longitudinal axis relative to the first member.

The orthopedic implant further includes a third member defining a first wall disposed for sealed engagement with the first wall of the second member. The first wall of the third member defines at least a portion of the chamber and a second graft containment cavity. The chamber is separate from the second graft containment cavity. The third member is configured for movement along the longitudinal axis relative to the second member. The members are disposed in a telescopic arrangement such that the sealed engagement of the members facilitates expansion of the members under a fluid pressure in the chamber for movement between a first orientation and a second orientation such that the first member and the third member are disposed to engage adjacent bone surfaces.

In one embodiment, the orthopedic implant includes a flexible layer disposed circumferentially about the first wall of the members to define the chamber. The members and the flexible layer are expandable under a fluid pressure in the chamber for movement between a first orientation and a second orientation such that the first member and the third member are disposed to engage adjacent bone surfaces.

In one embodiment, an orthopedic implant system is provided, which includes a first cylinder defining a longitudinal axis, a first tubular portion, a second tubular portion and a transverse wall therebetween. The first tubular portion defines at least a portion of a chamber. The second tubular portion includes a plurality of openings and defines a first graft containment cavity. The chamber is separate from the first graft containment cavity by the transverse wall. The first cylinder further defines a fluid receiving port configured to communicate with the chamber. A second cylinder defines a first tubular portion disposed for sealed engagement with the first tubular portion of the first cylinder. The first tubular portion of the second cylinder defines at least a portion of the chamber. The second cylinder is configured for movement along the longitudinal axis relative to the first cylinder.

The orthopedic implant system further includes a third cylinder defining a first tubular portion. The first tubular portion of the third cylinder has an outer surface disposed for sealed engagement with the first tubular portion of the second cylinder and defining at least a portion of the chamber. The first tubular portion of the third cylinder including a plurality of openings and a second graft containment cavity. The chamber is separate from the second graft containment cavity. The third cylinder is configured for movement along the longitudinal axis relative to the second cylinder. The orthopedic implant system further includes bone graft configured for disposal in the first graft containment cavity and/or the second graft containment cavity. The cylinders are concentric with the longitudinal axis and disposed in a telescopic arrangement such that the sealed engagement of the cylinders facilitates expansion of the cylinders under a fluid pressure in the chamber for movement between a first orientation such that the cylinders are disposed in a nested configuration and a second orientation such that the first cylinder and the third cylinder are disposed to engage adjacent bone surfaces.

BRIEF DESCRIPTION OF THE DRAWINGS

The present disclosure will become more readily apparent from the specific description accompanied by the following drawings, in which.

Like reference numerals indicate similar parts throughout the figures.

DETAILED DESCRIPTION OF THE INVENTION

Figure 1:
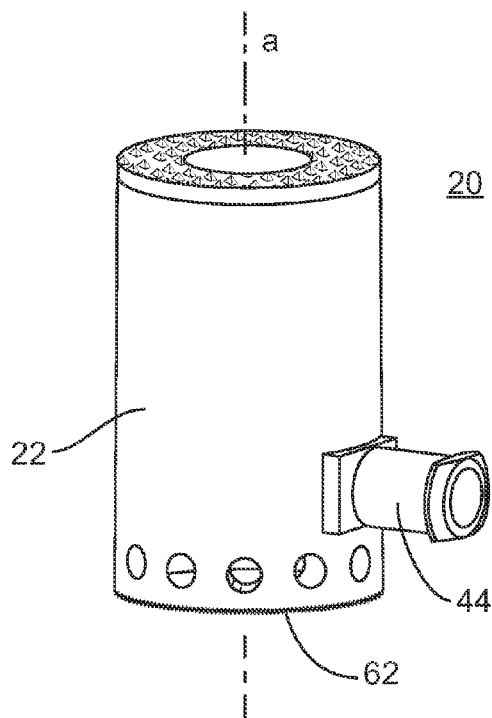
FIG. 1 is a perspective view of one embodiment of an orthopedic implant in accordance with the principles of the present disclosure.

The exemplary embodiments of the orthopedic implant system and related methods of use disclosed are discussed in terms of medical devices for the treatment of bone disorders and more particularly, in terms of an orthopedic implant system that includes members disposed in a telescopic arrangement that are expanded under fluid pressure to engage adjacent bone surfaces. It is envisioned that the orthopedic implant is deployed hydraulically. For example, such deployment can employ a fluid including cement, which hardens to a desired solid state over time. It is further envisioned that the telescopic arrangement of the orthopedic implant may include a nested tubular configuration that is relatively slidable and expandable axially, while circumferentially containing the fluid under pressure.

The present disclosure can be used with a corpectomy and/or discectomy such that the orthopedic implant is deployable with telescoping sections in a body space of a patient where all or a portion of a vertebral body and/or an intervertebral disc(s) is removed. It is envisioned that the present disclosure may be employed to treat spinal disorders such as, for example, degenerative disc disease, disc herniation, osteoporosis, spondylolisthesis, stenosis, scoliosis and other curvature abnormalities, kyphosis, tumor and fractures.

It is contemplated that the present disclosure may be employed with other osteal and bone related applications, including those associated with diagnostics and therapeutics. It is further contemplated that the disclosed orthopedic implant system may be employed in a surgical treatment with a patient in a prone or supine position, and/or employ various surgical approaches to the spine, including anterior, posterior, posterior mid-line, lateral, postero-lateral, and/or antero-lateral approaches, and in other body regions. The present disclosure may also be alternatively employed with procedures for treating the lumbar, cervical, thoracic and pelvic regions of a spinal column. The system and methods of the present disclosure may also be used on animals, bone models and other non-living substrates, such as, for example, in training, testing and demonstration.

The present disclosure may be understood more readily by reference to the following detailed description of the disclosure taken in connection with the accompanying drawing figures, which form a part of this disclosure. It is to be understood that this disclosure is not limited to the specific devices, methods, conditions or parameters described and/or shown herein, and that the terminology used herein is for the purpose of describing particular embodiments by way of example only and is not intended to be limiting of the claimed disclosure. Also, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, left and right, are for illustrative purposes only and can be varied within the scope of the disclosure. For example, the references "upper" and "lower" are relative and used only in the context to the other, and are not necessarily "superior" and "inferior".

Figure 2:
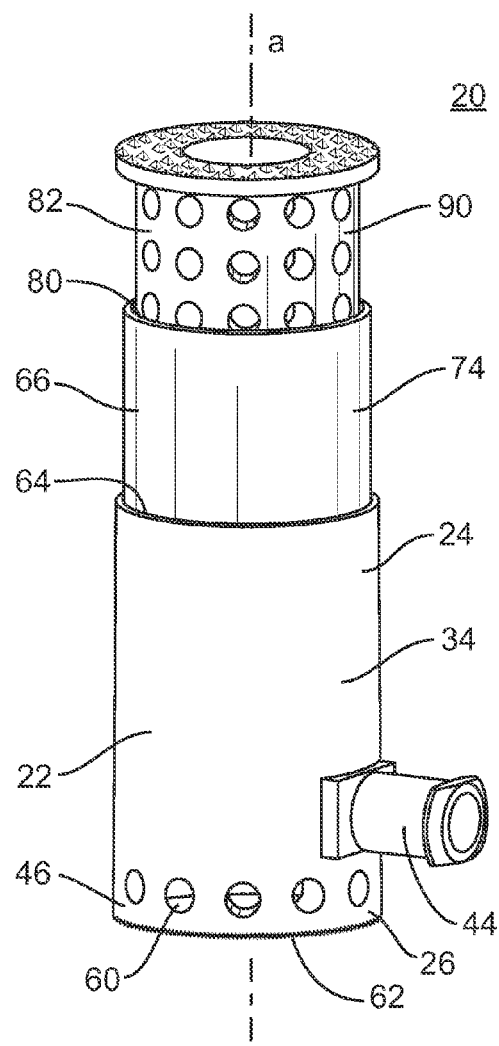
FIG. 2 is a perspective view of the orthopedic implant shown in FIG. 1.
Figure 3:
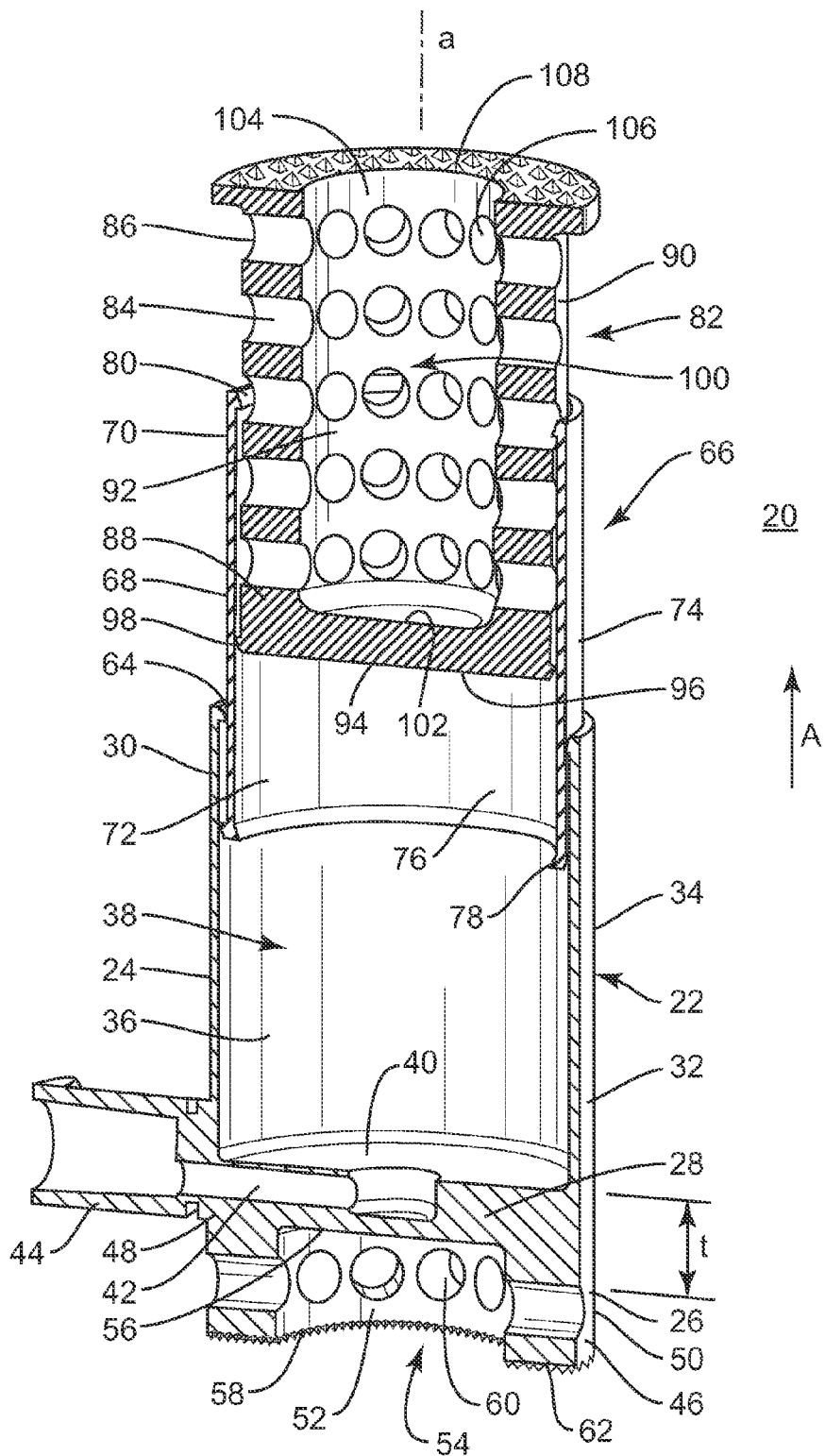
FIG. 3 is a perspective view in cross section of the orthopedic implant shown in FIG. 1.

The following discussion includes a description of an orthopedic implant system and related methods of employing the orthopedic implant system in accordance with the principles of the present disclosure. Alternate embodiments are also disclosed. Reference will now be made in detail to the exemplary embodiments of the present disclosure, which are illustrated in the accompanying figures. Turning now to FIGS. 1-3, there is illustrated components of an orthopedic implant system including an orthopedic implant 20 in accordance with the principles of the present disclosure.

The components of the orthopedic implant system are fabricated from materials suitable for medical applications, including metals, polymers, ceramics, biocompatible materials, bone, autograft, allograft and/or their composites, depending on the particular application and/or preference of a medical practitioner. For example, the components of the orthopedic implant system, individually or collectively, and which may be monolithically formed or integrally connected, can be fabricated from materials such as stainless steel, stainless steel alloys, titanium, titanium alloys, super-elastic titanium alloys, cobalt-chrome alloys, shape memory materials, such as super-elastic metallic alloys (e.g., Nitinol, super-elastic plastic metals, such as GUM METAL® manufactured by Toyota Material Incorporated of Japan), thermoplastics such as polyaryletherketone (PAEK) including polyetheretherketone (PEEK), polyetherketoneketone (PEKK) and polyetherketone (PEK), carbon-PEEK composites, PEEK-$BaSO_4$ polymeric rubbers, biocompatible materials such as polymers including plastics, metals, ceramics and composites thereof, rigid polymers including polyphenylene, polyamide, polyimide, polyetherimide, polyethylene, and epoxy. Various components of the orthopedic implant system may have material composites, including the above materials, to achieve various desired characteristics such as strength, rigidity, elasticity, compliance, biomechanical performance, durability and radiolucency or imaging preference.

The orthopedic implant system is configured for use with a surgical treatment, such as, for example, a corpectomy. It is contemplated that orthopedic implant 20 is deployed into a body space of a patient where all or only a portion of a vertebral body is removed. Orthopedic implant 20 is deployed by an expanding medium, such as, for example, hydraulically by a fluid under pressure, as will be described. It is envisioned that orthopedic implant 20 may be alternatively deployed by a biasing mechanism such as a spring or other mechanical structure.

Orthopedic implant 20 includes a first member, such as, for example, a cylinder 22 that defines a longitudinal axis a. Cylinder 22 defines a first wall, such as, for example, a tubular portion 24 and a second wall, such as, for example, a tubular portion 26. Cylinder 22 includes a transverse wall 28 disposed between tubular portion 24 and tubular portion 26. Tubular portion 24 and tubular portion 26 are disposed in a concentric orientation with longitudinal axis a. It is envisioned that tubular portion 24 and/or tubular portion 26 may be offset, staggered or disposed at an angle from longitudinal axis a.

Tubular portion 24 extends from a first end 30 to a second end 32 that connects with transverse wall 28. Tubular portion 24 has an outer surface 34 that defines an outer circumference of tubular portion 24 and an inner surface 36 that defines an inner circumference thereof. Surfaces 34, 36 are smooth or even and tubular portion 24 has a cylindrical cross-section. It is envisioned that surfaces 34, 36 may be rough, textured, porous, semi-porous, dimpled and/or polished. It is further envisioned that the cross-sectional geometry of tubular portion 24 may have various configurations, such as, for example, round, oval, oblong, triangular, polygonal having planar or arcuate sides, irregular, uniform, non-uniform, consistent, variable, horseshoe shape, U-shape or kidney bean shape.

Inner surface 36 defines a portion of a chamber 38 with a first surface 40 of transverse wall 28. Chamber 38 has a cylindrical cross-section and is configured for receipt of a fluid under pressure for hydraulic deployment of orthopedic implant 20. Surfaces 36, 40 define at least a portion of chamber 38 to contain the pressurized fluid that is laterally constrained by tubular portion 24 and to facilitate axial expansion of the components of orthopedic implant 20, relative to longitudinal axis a. It is contemplated that the cross-sectional geometry of chamber 38 may have various configurations, such as, for example, round, oval, oblong, triangular, polygonal, irregular, uniform, non-uniform, consistent or variable, and may be uniform or alternative to the cross-sectional geometry of tubular portion 24 via internal structure or components.

Transverse wall 28 defines a thickness t, which includes a lumen 42 connected with a fluid receiving port 44 of cylinder 22. Lumen 42 has a transverse orientation relative to longitudinal axis a and facilitates communication between port 44 and chamber 38. Port 44 is connected with a fluid supply source (not shown) that delivers pressurized fluid through lumen 42 and into chamber 38 for expansion of orthopedic implant 20. It is envisioned that the fluid supply source may provide fluid, such as, for example, bio-compatible materials, gases such as air, liquids, such as sterile water, saline, curable materials including cement such as polymethylmethacrylate (PMMA) cement and other synthetic bone cements, mineral compositions, polymers including curable polymers formed via polymeric reaction and bioceramics. It is contemplated that port 44 may include a threaded connection or quick disconnect coupling with the fluid supply source. It is further contemplated that expansion of orthopedic implant 20 may include inflation. In one embodiment, a low durometer rubber is delivered into chamber 38 for expansion of orthopedic implant 20 such that implant 20 has a flexible configuration that provides a dynamic/motion sparing feature when implanted with vertebrae, in for example, an arthroplasty application and/or a fixation application that includes motion.

Tubular portion 26 extends from a first end 46 to a second end 48 that connects with transverse wall 28. Tubular portion 26 has an outer surface 50 that defines an outer circumference of tubular portion 26 and an inner surface 52 that defines an inner circumference thereof. Surfaces 50, 52 are smooth or even and tubular portion 26 has a cylindrical cross-section. Outer surface 50 has a uniform circumference with outer surface 34. Outer surface 50 may be offset from outer surface 34. It is envisioned that surfaces 50, 52 may be rough, textured, porous, semi-porous, dimpled and/or polished. It is further envisioned that the cross-sectional geometry of tubular portion 26 may have various configurations, such as, for example, round, oval, oblong, triangular, polygonal having planar or arcuate sides, irregular, uniform, non-uniform, consistent or variable.

Inner surface 52 defines a first graft containment cavity 54 with a second surface 56 of transverse wall 28. Transverse wall 28 separates chamber 38 from cavity 54 such that chamber 38 and cavity 54 are not in fluid communication. As such, the pressurized fluid disposed in chamber 38 is prevented from flowing into cavity 54 and bone graft and/or other materials disposed in cavity 54 are prevented from flowing into chamber 38 to effectively seal the respective regions.

Graft containment cavity 54 has a cylindrical cross-section and is configured for receipt of bone graft (not shown) and/or other materials, described herein, for employment in a fixation or fusion treatment used for example, in connection with a corpectomy. Tubular portion 26 defines an axially oriented opening 58 and a plurality of laterally oriented openings 60. Openings 58, 60 are configured to facilitate the flow of bone graft and/or other materials from graft containment cavity 54 exterior to tubular portion 26 and adjacent vertebrae, as will be discussed, to promote new bone growth, joint immobilization, therapy and/or treatment. It is contemplated that tubular portion 26 may define one or a plurality of openings. Openings 58, 60 can be oriented and facing a disc space and/or vertebrae. It is further contemplated that the cross-sectional geometry of the openings of tubular portion 26 may have various configurations, such as, for example, round, oval, oblong, triangular, polygonal, angularly directed relative to longitudinal axis a, irregular, uniform, non-uniform, consistent or variable.

In one embodiment, cavity 54 may include therapeutic polynucleotides or polypeptides and bone growth promoting material, which can be packed or otherwise disposed therein. Cavity 54 may also include at least one agent including biocompatible materials, such as, for example, biocompatible metals and/or rigid polymers, such as, titanium elements, metal powders of titanium or titanium compositions, sterile bone materials, such as allograft or xenograft materials, synthetic bone materials such as coral and calcium compositions, such as hydroxyapatite, calcium phosphate and calcium sulfite, biologically active agents, for example, biologically active agents coated onto the exterior of orthopedic implant 20 and/or applied thereto for gradual release such as by blending in a bioresorbable polymer that releases the biologically active agent or agents in an appropriate time dependent fashion as the polymer degrades within the patient. Suitable biologically active agents include, for example, bone morphogenic protein (BMP) and cytokines.

Cavity 54 may be a reservoir configured as a drug depot with medication for pain and may include antibiotics and/or therapeutics. It is envisioned that the cavity 54 contains active agents and may include one or a plurality of therapeutic agents and/or pharmacological agents for release, including sustained release, into the lumbo-sacral region to treat, for example, pain, inflammation and degeneration. The agents may include pharmacological agents, such as, for example, antibiotics, anti-inflammatory drugs including but not limited to steroids, anti-viral and anti-retroviral compounds, therapeutic proteins or peptides, therapeutic nucleic acids (as naked plasmid or a component of an integrating or non-integrating gene therapy vector system), and combinations thereof.

The agent may also include analgesics or anesthetics such as acetic acid derivatives, COX-2 selective inhibitors, COX-2 inhibitors, enolic acid derivatives, propionic acid derivatives, salicylic acid derivatives, opioids, opioid/nonopioid combination products, adjuvant analgesics, and general and regional/local anesthetics.

The agent may also include antibiotics such as, for example, amoxicillin, beta-lactamases, aminoglycosides, beta-lactam (glycopeptide), clindamycin, chloramphenicol, cephalosporins, ciprofloxacin, erythromycin, fluoroquinolones, macrolides, metronidazole, penicillins, quinolones, rapamycin, rifampin, streptomycin, sulfonamide, tetracyclines, trimethoprim, trimethoprim-sulfamthoxazole, and vancomycin.

The agent may also include immunosuppressives agents, such as, for example, steroids, cyclosporine, cyclosporine analogs, cyclophosphamide, methylprednisone, prednisone, azathioprine, FK-506, 15-deoxyspergualin, prednisolone, methotrexate, thalidomide, methoxsalen, rapamycin, leflunomide, mizoribine (Bredinin™), brequinar, deoxyspergualin, and azaspirane (SKF 105685), Orthoclone OKT™ 3 (muromonab-CD3). Sandimmune™, Neoral™, Sangdya™ (cyclosporine), Prograf™ (FK506, tacrolimus), Cellcept™ (mycophenolate motefil, of which the active metabolite is mycophenolic acid), Imuran™ (azathioprine), glucocorticosteroids, adrenocortical steroids such as Deltasone™ (prednisone) and Hydeltrasol™ (prednisolone), Folex™ and Mexate™ (methotrxate), Oxsoralen-Ultra™ (methoxsalen) and Rapamuen™ (sirolimus).

First end 46 defines an axial face 62 that is configured to engage a vertebral surface, which may include soft tissue and/or cartilage. Axial face 62 includes a gripping surface to facilitate fixation with a vertebral surface. The gripping surface may be knurled, rough, textured, dimpled and/or include ribs, teeth and prongs, and/or may be coated with adhesive. In one embodiment, axial face 62 may extend across the perimeter of tubular portion 26 such that tubular portion 26 does not include an axial opening. It is envisioned that axial face 62 may be disposed at an angular orientation relative to longitudinal axis a.

First end 30 of tubular portion 24 includes a flange 64 disposed circumferentially thereabout and being configured for engagement with a second member, such as, for example, a cylinder 66. Cylinder 66 defines a first wall, such as, for example, a tubular portion 68. Tubular portion 68 is disposed in a concentric orientation with longitudinal axis a. It is envisioned that tubular portion 68 may be offset, staggered or disposed at an angle from longitudinal axis a.

Tubular portion 68 extends from a first open end 70 to a second open end 72. Tubular portion 68 has an outer surface 74 that defines an outer circumference of tubular portion 68 and an inner surface 76 that defines an inner circumference thereof. Surfaces 74, 76 are smooth or even and tubular portion 68 has a cylindrical cross-section. It is envisioned that surfaces 74, 76 may be rough, textured, porous, semi-porous, dimpled and/or polished. It is further envisioned that the cross-sectional geometry of tubular portion 68 may have various configurations, such as, for example, round, oval, oblong, triangular, polygonal having planar or arcuate sides, irregular, uniform, non-uniform, consistent or variable.

Flange 64 engages smooth outer surface 74 in a sealed configuration to prevent the flow of the pressurized fluid out of chamber 38. This configuration facilitates slidable movement of flange 64 along outer surface 74 such that cylinder 66 slidably moves, under the hydraulic pressure provided from the pressurized fluid, along longitudinal axis a in the direction shown by arrow A in FIG. 3, relative to cylinder 22. It is contemplated that flange 64 may include a gasket, membrane and/or lubricant to enhance sealing engagement with outer surface 74 and facilitate relative slidable movement of cylinders 22, 66.

Inner surface 76 defines a portion of a chamber 38 to contain the pressurized fluid that is laterally constrained by tubular portion 68 and to facilitate axial expansion of the components of orthopedic implant 20, relative to longitudinal axis a. Second end 72 includes a flange 78 disposed circumferentially thereabout and being configured for engagement with cylinder 22. Flange 78 engages smooth inner surface 36 in a sealed configuration to prevent the flow of the pressurized fluid out of chamber 38. This configuration facilitates slidable movement of flange 78 along inner surface 36 such that cylinder 66 slidably moves, under the hydraulic pressure provided from the pressurized fluid, along longitudinal axis a in the direction shown by arrow A, relative to cylinder 22. It is contemplated that flange 78 may include a gasket, membrane and/or lubricant to enhance sealing engagement with inner surface 36 and facilitate relative slidable movement of cylinders 22, 66.

Flange 78 is slidable along inner surface 36 between a first position (FIG. 1) such that flange 78 engages surface 40 and a second position (not shown) such that flange 78 engages flange 64 and is prevented from further axial movement in the direction of arrow A. This configuration allows the height and positioning of orthopedic implant 20 to be selectively adjusted according to the body space dimension, for example, the size of the space where vertebrae has been removed and/or a desired amount of distraction for vertebrae. It is contemplated that flange 78 may be fixed and/or locked with flange 64.

First end 70 of tubular portion 68 includes a flange 80 disposed circumferentially thereabout and being configured for engagement with a third member, such as, for example, a cylinder 82. Cylinder 82 defines a first wall, such as, for example, a tubular portion 84. Tubular portion 84 is disposed in a concentric orientation with longitudinal axis a. It is envisioned that tubular portion 84 may be offset, staggered or disposed at an angle from longitudinal axis a.

Tubular portion 84 extends from a first end 86 to a second end 88. Tubular portion 84 has an outer surface 90 that defines an outer circumference of tubular portion 84 and an inner surface 92 that defines an inner circumference thereof. Surfaces 90, 92 are smooth or even and tubular portion 84 has a cylindrical cross-section. It is envisioned that surfaces 90, 92 may be rough, textured, porous, semi-porous, dimpled and/or polished. It is further envisioned that the cross-sectional geometry of tubular portion 84 may have various configurations, such as, for example, round, oval, oblong, triangular, polygonal with planar or arcuate sides, irregular, uniform, non-uniform, consistent or variable.

Tubular portion 84 includes a transverse wall 94 that defines a transverse face 96 of outer surface 90. Transverse face 96 defines a portion of chamber 38 for containment of the pressurized fluid to facilitate axial expansion of the components of orthopedic implant 20, relative to longitudinal axis a. Second end 88 includes a flange 98 disposed circumferentially thereabout and being configured for engagement with cylinder 66. Flange 98 engages smooth inner surface 76 in a sealed configuration to prevent the flow of the pressurized fluid out of chamber 38. This configuration facilitates slidable movement of flange 98 along inner surface 76 such that cylinder 82 slidably moves, under the hydraulic pressure provided from the pressurized fluid, along longitudinal axis a in the direction shown by arrow A, relative to cylinder 66. It is contemplated that flange 98 may include a gasket, membrane and/or lubricant to enhance sealing engagement with inner surface 76 and facilitate relative slidable movement of cylinders 66, 82.

Flange 98 is slidable along inner surface 76 between a first position (FIG. 1) such that flange 98 engages surface 40 and a second position (not shown) such that flange 98 engages flange 80 and is prevented from further axial movement in the direction of arrow A. This configuration allows the height and positioning of orthopedic implant 20 to be selectively adjusted according to the body space dimension, for example, the size of the space where vertebrae has been removed and/or a desired amount of distraction for vertebrae. It is contemplated that flange 98 may be fixed and/or locked with flange 80.

Inner surface 92 defines a second graft containment cavity 100 with a second surface 102 of transverse wall 94. Transverse wall 94 separates chamber 38 from cavity 100 such that chamber 38 and graft containment cavity 100 are not in fluid communication. As such, the pressurized fluid disposed in chamber 38 is prevented from flowing into graft containment cavity 100 and bone graft and/or other materials disposed in graft containment cavity 100 are prevented from flowing into chamber 38 to effectively seal the respective regions.

Graft containment cavity 100 has a cylindrical cross-section and is configured for receipt of bone graft (not shown) and/or other materials such as those described with regard to cavity 54, for employment in a fixation or fusion treatment used for example, in connection with a corpectomy. Tubular portion 84 defines an axially oriented opening 104 and a plurality of laterally oriented openings 106. Openings 104, 106 are configured to facilitate the flow of bone graft and/or other materials from graft containment cavity 100 exterior to tubular portion 84 and adjacent vertebrae, as will be discussed, to promote new bone growth and fusion of the vertebrae. It is contemplated that tubular portion 84 may define one or a plurality of openings. It is further contemplated that the cross-sectional geometry of the openings of tubular portion 84 may have various configurations, such as, for example, round, oval, oblong, triangular, polygonal, angularly directed relative to longitudinal axis a, irregular, uniform, non-uniform, consistent or variable.

First end 86 defines an axial face 108 that is configured to engage a vertebral surface, which may include soft tissue and/or cartilage. Axial face 108 includes a gripping surface to facilitate fixation with a vertebral surface. The gripping surface may be knurled, rough, textured, porous, semi-porous, dimpled and/or include ribs, teeth and prongs, and/or may be coated with adhesive. In one embodiment, axial face 108 may extend across the perimeter of tubular portion 84 such that tubular portion 84 does not include an axial opening. It is envisioned that axial face 108 may be disposed at an angular orientation relative to longitudinal axis a.

Orthopedic implant 20 includes relatively movable cylinders 22, 66, 82 that are concentric with longitudinal axis a and disposed in a telescopic arrangement for delivery and implantation with a surgical site. The sealed engagement of cylinders 22, 66, 82 facilitates expansion of cylinders 22, 66, 82 under a fluid pressure in chamber 38 for movement between a first orientation (FIG. 1) such that cylinders 22, 66, 82 are disposed in a nested configuration and a second orientation (FIG. 2) such that cylinder 22 and cylinder 82 are disposed to engage adjacent bone surfaces, as will be described, to restore height and provide support in place of removed vertebrae, as well as provide bone graft and/or other materials to promote bone growth and facilitate fusion/fixation of vertebrae for an arthrodesis treatment.

In the nested configuration, cylinders 22, 66, 82 are seated concentrically such that substantially all of cylinder 82 is disposed within cylinder 66 and substantially all of cylinder 66 is disposed within cylinder 22. The fluid pressure provided to chamber 38 from the fluid pressure supply source is constrained by surfaces 40, 36, 76 resulting in pressure and an axial force distributed against surface 96, in the direction shown by arrow A. This axial expansion forces cylinder 82, in the direction shown by arrow A, away from surface 40 and to move relative to cylinder 66. Cylinder 82 is movable relative to cylinder 66 to a limit of engagement of flange 98 with flange 80.

Engagement of flanges 98, 80 and continued application of fluid pressure forces cylinder 66 away from surface 40, in the direction shown by arrow A, and to move relative to cylinder 22. Cylinder 66 is movable relative to cylinder 22 to a limit of engagement of flange 78 with flange 64. It is envisioned that the fluid pressure against the flange surfaces may contribute to expansion of the cylinders. It is further envisioned that one or all of cylinders 22, 66, 82 may be configured for low pressure expansion, high pressure expansion or a combination of cylinders each having a selected expansion pressure, which may be equal or different.

Orthopedic implant 20 is configured for axial expansion along longitudinal axis a. It is contemplated that implant 20 may expand in an arcuate configuration along a curvature relative to longitudinal axis a. It is further contemplated that all or only a portion of implant 20 may be arcuately expanded, such as one or all of cylinders 22, 66, 82 may include a curvature relative to longitudinal axis a.

Within the limits of expansion discussed above, implant 20 is expanded to the second orientation at a selected amount of spacing and/or distraction between vertebrae such that axial face 62 engages a first vertebral surface and axial surface 108 engages a second vertebral surface to restore vertebral spacing provide distraction and/or restore mechanical support function. In one embodiment, orthopedic implant 20 is expanded, as discussed herein, progressively and/or gradually to provide an implant configured to adapt to the growth of a patient including the vertebrae. Additional fluid can be delivered to chamber 38 over a period of time and/or several procedures to expand and increase the height of implant 20, for example, to accommodate the growth of a child. It is envisioned that the height of implant 20 may also be decreased over a period of time and/or several procedures to adapt to various conditions of a patient.

Referring to FIGS. 4-9, in assembly, operation and use, the orthopedic implant system including orthopedic implant 20 described with regard to FIGS. 1-3 is employed with a surgical procedure, such as, for example, a lumbar corpectomy for treatment of a spine of a patient including vertebrae V. The orthopedic implant system may also be employed with other surgical procedures, such as, for example, discectomy, laminectomy, fusion, laminotomy, laminectomy, nerve root retraction, foramenotomy, facetectomy, decompression, spinal nucleus or disc replacement and bone graft and implantable prosthetics including plates, rods, and bone engaging fasteners for securement of orthopedic implant 20.

Figure 4:
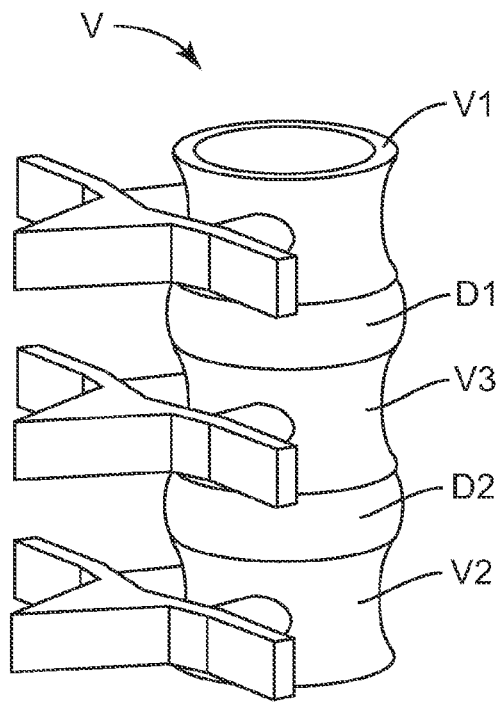
FIG. 4 is a perspective view of vertebrae at a surgical site.

The orthopedic implant system is employed with a lumbar corpectomy including surgical arthrodesis, such as, for example, fusion to immobilize a joint for treatment of an applicable condition or injury of an affected section of a spinal column and adjacent areas within a body. For example, vertebrae V includes a first vertebrae V1 and a second vertebrae V2. A diseased and/or damaged vertebrae V3 and intervertebral discs D1, D2 are disposed between vertebrae V1 and vertebrae V2, as shown in FIG. 4. It is contemplated that the orthopedic implant system is configured for insertion with a vertebral space to space apart articular joint surfaces, provide support and maximize stabilization of vertebrae V.

Figure 5:
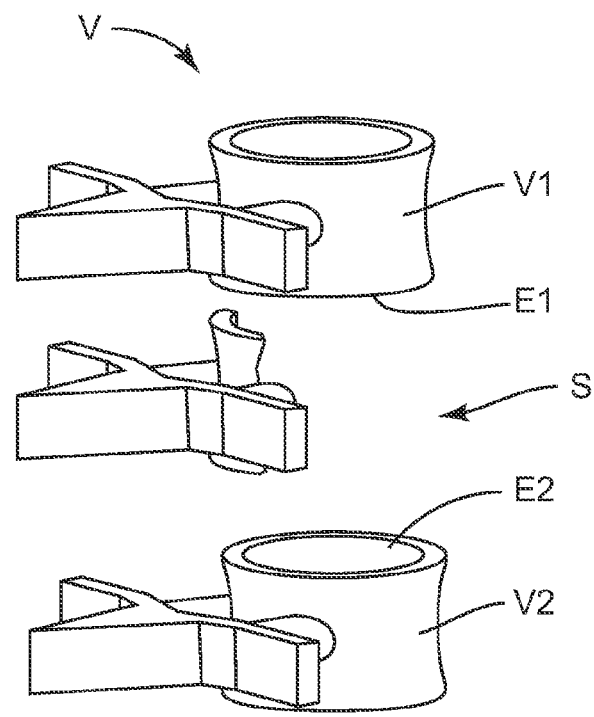
FIG. 5 is a perspective view of the vertebrae shown in FIG. 4.

In use, to treat the affected section of vertebrae V, a medical practitioner obtains access to a surgical site including vertebrae V in any appropriate manner, such as through incision and retraction of tissues. It is envisioned that the orthopedic implant system may be used in any existing surgical method or technique including open surgery, mini-open surgery, minimally invasive surgery and percutaneous surgical implantation, whereby vertebrae V is accessed through a mini-incision, or sleeve that provides a protected passageway to the area. Once access to the surgical site is obtained, corpectomy is performed for treating the spine disorder. The diseased and/or damaged portion of vertebrae V3, and diseased and/or damaged intervertebral discs D1, D2 are removed to create a vertebral space S, as shown in FIG. 5.

Figure 6:
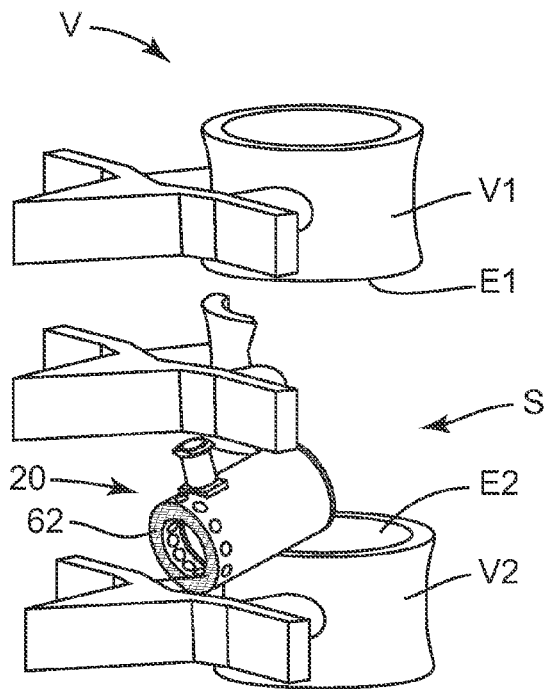
FIG. 6 is a perspective view of the orthopedic implant shown in FIG. 1 and the vertebrae shown in FIG. 5.
Figure 7:
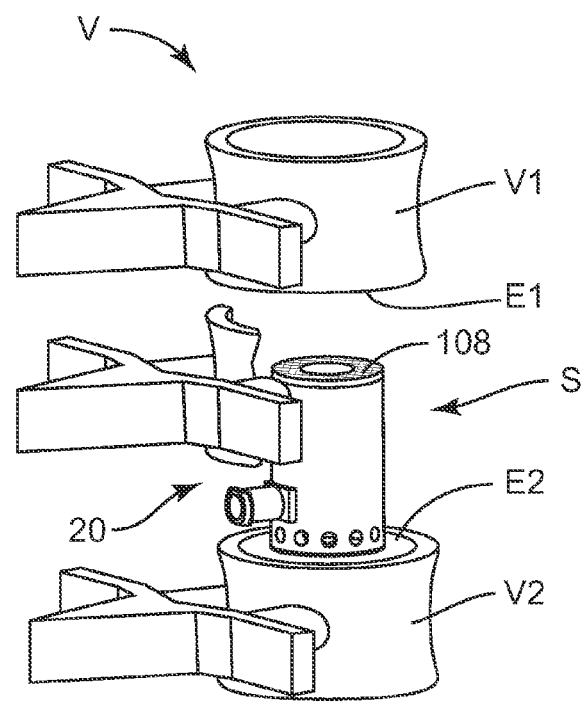
FIG. 7 is a perspective view of the orthopedic implant shown in FIG. 1 and the vertebrae shown in FIG. 5.

A preparation instrument (not shown) is employed to remove disc tissue, fluids, adjacent tissues and/or bone, and scrape and/or remove tissue from endplates surfaces E1, E2, of vertebrae V1, V2 respectively. Orthopedic implant 20 is provided with bone graft and/or other materials as described above in cavities 54, 100 to promote new bone growth and fusion to treat the affected section of vertebrae V. Orthopedic implant 20 is delivered to the surgical site of vertebrae V with a delivery instrument including a driver (not shown) via the protected passageway for the arthrodesis treatment. The driver delivers orthopedic implant 20 into the prepared vertebral space S, between vertebrae V1 and vertebrae V2, according to the requirements of a particular surgical application, as shown in FIGS. 6 and 7.

Orthopedic implant 20 is manipulated such that axial face 62 engages endplate surface E2. The gripping surface of face 62 penetrates and fixes with endplate surface E2. Orthopedic implant 20 is positioned in the first orientation (FIG. 1) with endplate surface E2, described above, such that cylinders 22, 66, 82 are disposed in a nested configuration.

Figure 8:
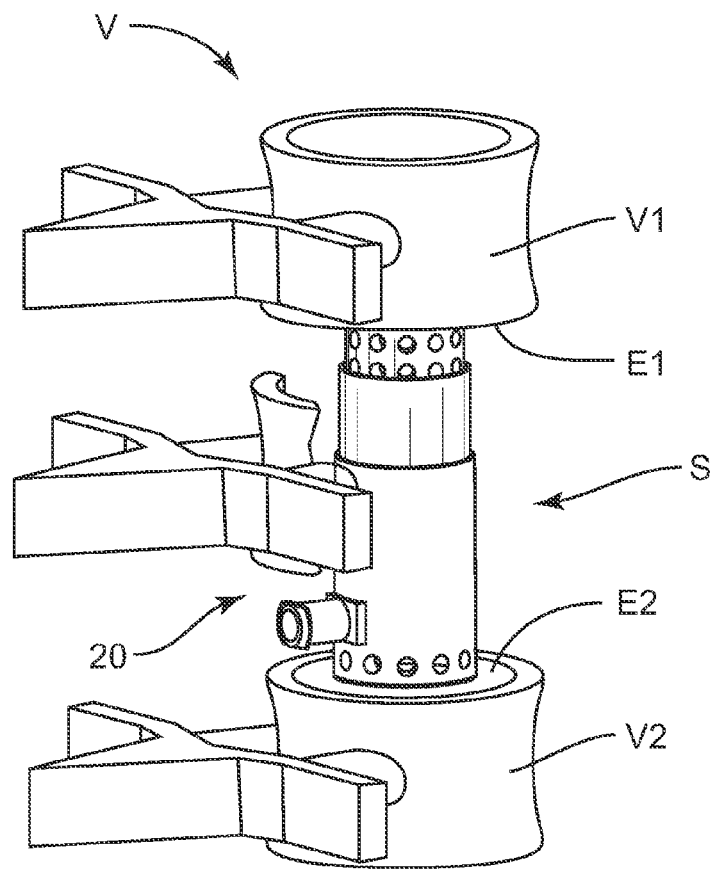
FIG. 8 is a perspective view of the orthopedic implant shown in FIG. 1 and the vertebrae shown in FIG. 5.
Figure 9:
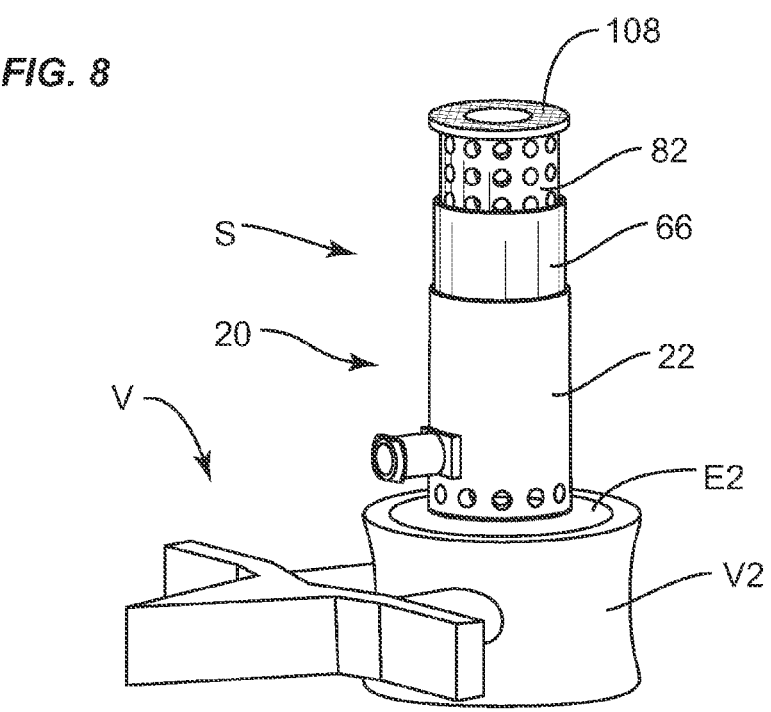
FIG. 9 is a perspective view of the orthopedic implant shown in FIG. 1 and a lower vertebrae at the surgical site shown in FIG. 5.
Figure 10:
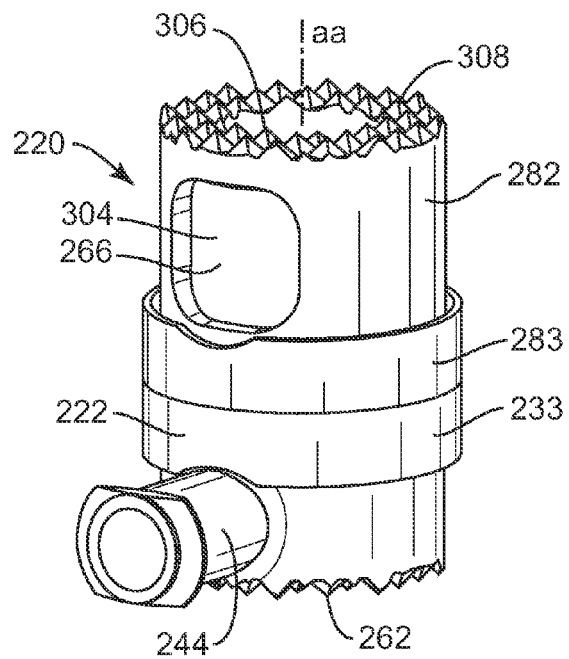
FIG. 10 is a perspective view of one embodiment of the orthopedic implant shown in FIG. 1.
Figure 11:
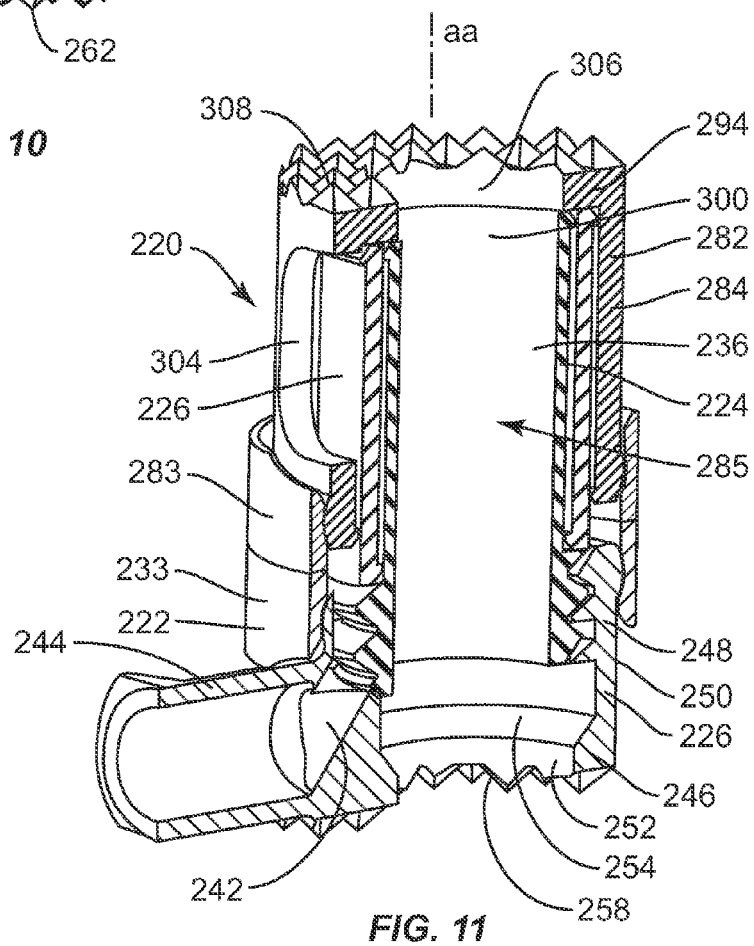
FIG. 11 is a perspective view in cross section of the orthopedic implant shown in FIG. 10.
Figure 12:
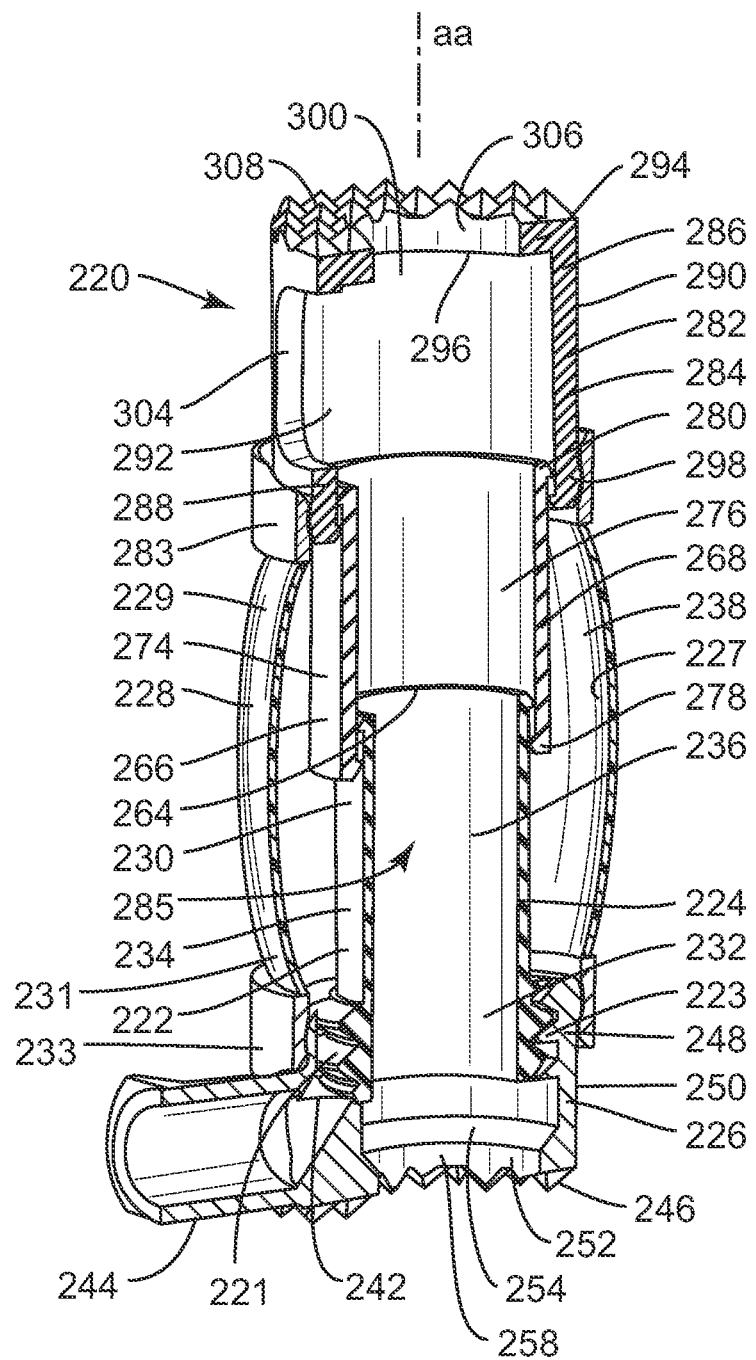
FIG. 12 is a perspective view in cross section of the orthopedic implant shown in FIG. 10.
Figure 13:
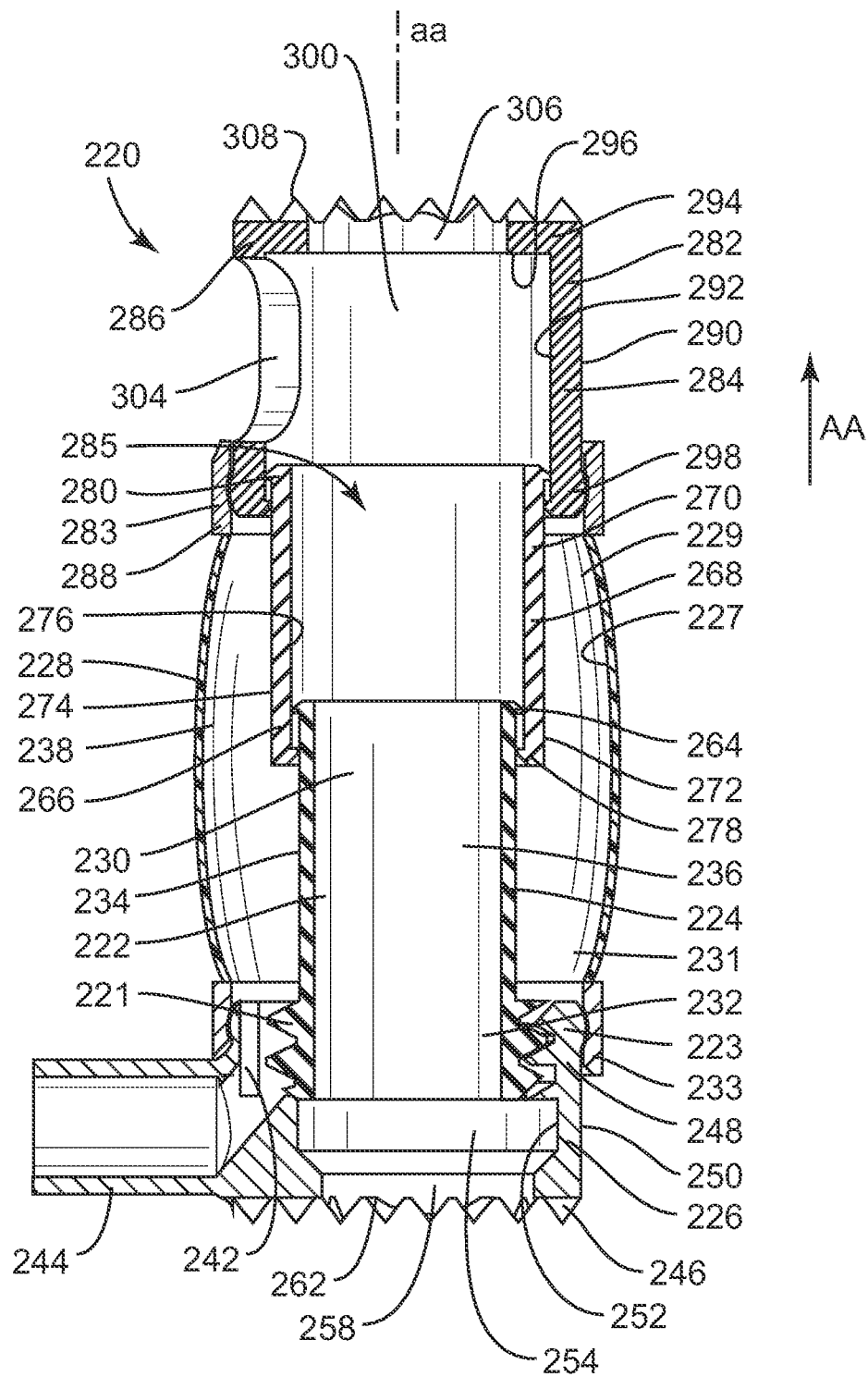
FIG. 13 is a side view in cross section of the orthopedic implant shown in FIG. 10.

Fluid pressure is provided to chamber 38 from the fluid pressure supply source and an axial force is distributed against surface 96, in the direction shown by arrow A in FIG. 3. This axial force expands orthopedic implant 20, as described above, to the second orientation at a selected amount of spacing and/or distraction of vertebral space S and is configured such that axial face 62 maintains engagement with endplate surface E2 of vertebrae V2 and axial surface 108 engages endplate surface E1 of vertebrae V1 to restore vertebral spacing and mechanical support function, as shown in FIG. 8. FIG. 9 shows orthopedic implant 20 with cylinders 22, 66, 82 expanded (portions of vertebrae V are not shown for illustration purposes).

Orthopedic implant 20 engages and spaces apart the opposing endplate surfaces E1, E2 and is secured within vertebral space S to stabilize and immobilize portions of vertebrae V in connection with bone growth for fusion and fixation of vertebrae V1, V2. Fixation of orthopedic implant 20 with endplate surfaces E1, E2 may be facilitated by the resistance provided by the joint space and/or engagement with endplate surfaces E1, E2. It is contemplated that orthopedic implant 20 may engage only one endplate. It is further contemplated that additional bone graft and/or other materials may be applied to areas of the surgical site to promote bone growth. The orthopedic implant system can be delivered or implanted as a pre-assembled device or can be assembled in situ. The orthopedic implant system may be completely or partially revised, removed or replaced in situ. It is envisioned that one or all of the components of the orthopedic implant system can be delivered to the surgical site via mechanical manipulation and/or a free hand technique.

In one embodiment, orthopedic implant 20 may include fastening elements, which may include locking structure, configured for fixation with vertebrae V1, V2 to secure joint surfaces and provide complementary stabilization and immobilization to the vertebral region. It is envisioned that locking structure may include fastening elements such as, for example, rods, plates, clips, hooks, adhesives and/or flanges. It is further envisioned that the orthopedic implant system can be used with screws to enhance fixation. It is contemplated that the orthopedic implant system and any screws and attachments may be coated with an osteoconductive material such as hydroxyapatite and/or osteoinductive agent such as a bone morphogenic protein for enhanced bony fixation to the treated area. The orthopedic implant system can be made of radiolucent materials such as polymers. Radiomarkers may be included for identification under x-ray, fluoroscopy, CT or other imaging techniques.

In one embodiment, the orthopedic implant system includes a plurality of orthopedic implants 20. It is contemplated that employing the plurality of implants 20 can optimize the amount vertebral space S can be spaced apart such that the joint spacing dimension can be preselected. The plurality of implants 20 can be oriented in a side by side engagement, spaced apart and/or staggered.

It is envisioned that the use of microsurgical and image guided technologies may be employed to access, view and repair spinal deterioration or damage, with the aid of the orthopedic implant system. Upon completion of the procedure, the surgical instruments and assemblies are removed and the incision is closed.

In one embodiment, as shown in FIGS. 10-13, the orthopedic implant system, similar to the system and method described with regard to FIGS. 1-9, includes an orthopedic implant 220. Orthopedic implant 220 includes a first member, such as, for example, a cylinder 222 that defines a longitudinal axis aa. Tubular portion 224 has threads 221 that mate with threads 223 of tubular portion 226 for a fixed connection of portions 224, 226. It is envisioned that tubular portion 224 and/or tubular portion 226 may be offset, staggered or disposed at an angle from longitudinal axis aa.

Tubular portion 224 extends from a first end 230 to a second end 232. Tubular portion 224 has an outer surface 234 that defines an outer circumference of tubular portion 224 and an inner surface 236 that defines an inner circumference thereof. Surfaces 234, 236 are smooth or even and tubular portion 224 has a cylindrical cross-section.

Outer surface 234 defines a portion of a chamber 238 with a flexible layer, such as, for example, balloon 228. Balloon 228 is disposed circumferentially about tubular portion 224 and includes an inner surface 227 that defines chamber 238. Balloon 228 extends from a first end 229 to a second end 231. Second end 231 is connected with a collar 233 of cylinder 222.

Chamber 238 is disposed circumferentially about cylinder 222 and has a toroid cross-section. Chamber 238 is configured for receipt of a fluid under pressure for hydraulic deployment of orthopedic implant 220. Surfaces 234, 227 define at least a portion of chamber 238 to contain the pressurized fluid that is laterally constrained by tubular portion 224 and balloon 228 and to facilitate axial expansion of the components of orthopedic implant 220, relative to longitudinal axis aa. It is contemplated that balloon 228 is expandable axially with no radial expansion. It is further contemplated that balloon 228 may include expansion having a radial component.

It is envisioned that the flexible layer may be resilient, low compliant, high compliant, non-compliant, low pressure, high pressure, and/or include one or a plurality of layers such as a laminate. It is contemplated that the cross-sectional geometry of chamber 238 may have various configurations, such as, for example, round, oval, oblong, triangular, polygonal, irregular, uniform, non-uniform, consistent or variable. It is further contemplated that the flexible layer may be fabricated foam and/or include the materials described above and elastic materials such as, for example, urethane, polyurethane, latex, silicone, polyvinylchloride (PVC), Pebax and other elastomers, chemically resistant materials, nylon, polyethylene terephthalate (PET) and/or their composites.

Cylinder 222 includes a lumen 242 connected with a fluid receiving port 244. Lumen 242 has a transverse orientation relative to longitudinal axis aa and facilitates communication between port 244 and chamber 238. Port 244 is connected with a fluid supply source (not shown) that delivers pressurized fluid similar to those described herein, through lumen 242 and into chamber 238 for expansion of orthopedic implant 220.

Tubular portion 226 extends from a first end 246 to a second end 248. Tubular portion 226 has an outer surface 250 that defines an outer circumference of tubular portion 226 and an inner surface 252 that defines an inner circumference thereof. Surfaces 250, 252 are smooth or even and tubular portion 226 has a cylindrical cross-section.

Inner surface 252 defines a first graft containment cavity 254. Chamber 238 is separate from cavity 254 such that chamber 238 and cavity 254 are not in fluid communication. As such, the pressurized fluid disposed in chamber 238 is prevented from flowing into cavity 254 and bone graft and/or other materials disposed in cavity 254 are prevented from flowing into chamber 238 to effectively seal the respective regions.

Graft containment cavity 254 has a cylindrical cross-section and is configured for receipt of bone graft (not shown) and/or other materials, described herein, for employment in a fixation or fusion treatment used for example, in connection with a corpectomy. Tubular portion 226 defines an axially oriented opening 258. Opening 258 is configured to facilitate the flow of bone graft and/or other materials from graft containment cavity 254 exterior to tubular portion 226 and adjacent vertebrae, as discussed above, to promote new bone growth, joint immobilization, therapy and/or treatment. It is contemplated that tubular portion 226 may define one or a plurality of openings.

First end 246 defines an axial face 262 that is configured to engage a vertebral surface, which may include soft tissue and/or cartilage. Axial face 262 includes a gripping surface, similar to those described, to facilitate fixation with the vertebral surface.

First end 230 of tubular portion 224 includes a flange 264 disposed circumferentially thereabout and being configured for engagement with a second member, such as, for example, a cylinder 266. Cylinder 266 defines a first wall, such as, for example, a tubular portion 268. Tubular portion 268 is disposed in a concentric orientation with longitudinal axis aa. It is envisioned that tubular portion 268 may be offset, staggered or disposed at an angle from longitudinal axis aa.

Tubular portion 268 extends from a first open end 270 to a second open end 272. Tubular portion 268 has an outer surface 274 that defines an outer circumference of tubular portion 268 and an inner surface 276 that defines an inner circumference thereof. Surfaces 274, 276 are smooth or even and tubular portion 268 has a cylindrical cross-section.

Flange 264 engages smooth inner surface 276 in a sealed configuration. This configuration facilitates slidable movement of flange 264 along inner surface 276 such that cylinder 266 slidably moves, under the hydraulic pressure provided from the pressurized fluid, along longitudinal axis aa in the direction shown by arrow AA in FIG. 13, relative to cylinder 222.

Outer surface 274 defines a portion of a chamber 238 to contain the pressurized fluid that is laterally constrained by tubular portion 268 and balloon 228, and to facilitate axial expansion of the components of orthopedic implant 220, relative to longitudinal axis aa. Second end 272 includes a flange 278 disposed circumferentially thereabout and being configured for engagement with cylinder 222. Flange 278 engages smooth outer surface 234 in a sealed configuration to prevent the flow of the pressurized fluid out of chamber 238. This configuration facilitates slidable movement of flange 278 along outer surface 234 such that cylinder 266 slidably moves, under the hydraulic pressure provided from the pressurized fluid, along longitudinal axis aa in the direction shown by arrow AA, relative to cylinder 222.

Flange 278 is slidable along outer surface 234 between a first position (FIG. 11) such that flange 278 engages the portion of cylinder 222 adjacent threads 221, 223 and a second position (not shown) such that flange 278 engages flange 264 and is prevented from further axial movement in the direction of arrow AA. This configuration allows the height and positioning of orthopedic implant 220 to be selectively adjusted according to the body space dimension, for example, the size of the space where vertebrae has been removed and/or a desired amount of distraction for vertebrae.

First end 270 of tubular portion 268 includes a flange 280 disposed circumferentially thereabout and being configured for engagement with a third member, such as, for example, a cylinder 282. Cylinder 282 defines a first wall, such as, for example, a tubular portion 284. Tubular portion 284 is disposed in a concentric orientation with longitudinal axis aa. It is envisioned that tubular portion 284 may be offset, staggered or disposed at an angle from longitudinal axis aa. The inner surfaces of cylinders 222, 266, 284 define an interior cavity such as, for example, a cannulation 285 of orthopedic implant 220. Cannulation 285 and inner surface 227 of balloon 228 define the toroid cross section configuration of chamber 238.

Tubular portion 284 extends from a first end 286 to a second end 288. Tubular portion 284 has an outer surface 290 that defines an outer circumference of tubular portion 284 and an inner surface 292 that defines an inner circumference thereof. Surfaces 290, 292 are smooth or even and tubular portion 284 has a cylindrical cross-section. First end 229 of balloon 228 is connected with a collar 283 of cylinder 284. Collar 283 includes a portion of outer surface 290 that defines a portion of chamber 238 for containment of the pressurized fluid to facilitate axial expansion of the components of orthopedic implant 220, relative to longitudinal axis aa.

Tubular portion 284 includes a transverse wall 294 that defines a transverse face 296 of inner surface 292. Second end 288 includes a flange 298 disposed circumferentially thereabout and being configured for engagement with cylinder 266. Flange 298 engages smooth outer surface 274 in a sealed configuration to prevent the flow of the pressurized fluid out of chamber 238. This configuration facilitates slidable movement of flange 298 along outer surface 274 such that cylinder 282 slidably moves, under the hydraulic pressure provided from the pressurized fluid, along longitudinal axis aa in the direction shown by arrow AA, relative to cylinder 266.

Flange 298 is slidable along outer surface 274 between a first position (FIG. 11) such that flange 298 is disposed adjacent the portion of tubular portions 224, 226 including threads 221, 223 and a second position (not shown) such that flange 298 engages flange 280 and is prevented from further axial movement in the direction of arrow AA. This configuration allows the height and positioning of orthopedic implant 220 to be selectively adjusted according to the body space dimension, for example, the size of the space where vertebrae has been removed and/or a desired amount of distraction for vertebrae.

Inner surface 292 defines a second graft containment cavity 300 with transverse face 296. Collar 283 separates chamber 238 from cavity 300 such that chamber 238 and cavity 300 are not in fluid communication. As such, the pressurized fluid disposed in chamber 238 is prevented from flowing into cavity 300 and bone graft and/or other materials disposed in cavity 300 are prevented from flowing into chamber 238 to effectively seal the respective regions.

Graft containment cavity 300 has a cylindrical cross-section and is configured for receipt of bone graft (not shown) and/or other materials such as those described with regard to cavity 54, for employment in a fixation or fusion treatment used for example, in connection with a corpectomy. Tubular portion 284 defines a laterally oriented opening 304 and an axially oriented opening 306. Openings 304, 306 are configured to facilitate the flow of bone graft and/or other materials from graft containment cavity 300 exterior to tubular portion 284 and adjacent vertebrae to promote new bone growth and fusion of the vertebrae. It is contemplated that tubular portion 284 may define one or a plurality of openings. It is further contemplated that cannulation 285 may provide a pathway for bone graft and/or other materials between cavities 254, 300.

First end 286 defines an axial face 308 that is configured to engage a vertebral surface, which may include soft tissue and/or cartilage. Axial face 308 includes a gripping surface, similar to those described above, to facilitate fixation with a vertebral surface.

Orthopedic implant 220 includes relatively movable cylinders 222, 266, 282 that are concentric with longitudinal axis aa and disposed in a telescopic arrangement for delivery and implantation with a surgical site. Balloon 228 and the sealed engagement of cylinders 222, 266, 282 facilitate expansion of cylinders 222, 266, 282 under a fluid pressure in chamber 238 for movement between a first orientation (FIG. 11) such that cylinders 222, 266, 282 are disposed in a collapsed configuration and a second, inflated orientation (FIG. 12) such that cylinder 222 and cylinder 282 are disposed to engage adjacent bone surfaces, as described above, to restore height and provide support in place of removed vertebrae, as well as provide bone graft and/or other materials to promote bone growth and facilitate fusion/fixation of vertebrae for an arthrodesis treatment.

In the collapsed configuration, cylinders 222, 266, 282 are seated concentrically such that substantially all of cylinder 282 is disposed with cylinder 266 and substantially all of cylinder 266 is disposed within cylinder 222. Collar 283 is disposed in a flush engagement with collar 233. Collars 283, 233 enclose a collapsed balloon 228 within the portion of chamber 238 adjacent second end 232 of tubular portion 224. The fluid pressure provided to chamber 238 from the fluid pressure supply source is constrained by surfaces 234, 274, 290 resulting in an inflation pressure distributed against surface 227 of balloon 228. This causes axial expansion of cylinder 282, in the direction shown by arrow AA, away from second end 232 and to move relative to cylinder 266. As balloon 228 inflates, cylinder 282 is movable relative to cylinder 266 to a limit of engagement of flange 298 with flange 280.

Engagement of flanges 298, 280 and continued application of fluid pressure forces cylinder 266 away from second end 232, in the direction shown by arrow AA, and to move relative to cylinder 222. Cylinder 266 is movable relative to cylinder 222 to a limit of engagement of flange 278 with flange 264. It is envisioned that the fluid pressure against the flange surfaces may contribute to expansion of the cylinders.

Within the limits of expansion discussed above, implant 220 is expanded to the second orientation at a selected amount of spacing and/or distraction between vertebrae such that axial face 262 engages a first vertebral surface and axial surface 308 engages a second vertebral surface to restore vertebral spacing and the mechanical support function.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. An orthopedic implant comprising:
a first member defining a longitudinal axis, a first wall and a second wall, the first wall defining at least a portion of a chamber and the second wall defining a first axial face comprising an opening defining a first graft containment cavity, the second wall having a tubular configuration and further defining at least one lateral opening, the chamber being separate from the first graft containment cavity, wherein the first member defines a fluid receiving port configured to communicate with the chamber only, the first member includes a transverse wall separating the chamber and the first graft containment cavity, the transverse wall has a reservoir therein in communication with the chamber, and the implant comprises a lumen connecting the reservoir with the fluid receiving port; and
a second member defining a first wall having an outer surface configured to engage an inner surface of the first wall of the first member such that the first wall of the second member is disposed for sealed engagement with the first wall of the first member, the first wall of the second member defining at least a portion of the chamber, the second member being configured for movement along the longitudinal axis relative to the first member; and
a third member defining a first wall having an outer surface configured to engage an inner surface of the first wall of the second member such that the first wall of the third member is disposed for sealed engagement with the first wall of the second member, the first wall of the third member defining at least a portion of the chamber and a second axial face opposite the first axial face comprising an opening defining a second graft containment cavity, the chamber being separate from the second graft containment cavity, the third member being configured for movement along the longitudinal axis relative to the second member,
wherein the members are disposed in a telescopic arrangement such that the sealed engagement of the members facilitates expansion of the members under a fluid pressure in the chamber for movement between a first orientation and a second orientation such that the first member and the third member are disposed to engage adjacent bone surfaces.

2. The orthopedic implant of claim 1, wherein the first wall of the first member has a tubular configuration.

3. The orthopedic implant of claim 2, wherein the first tubular wall and the second tubular wall are concentric with the longitudinal axis.

4. The orthopedic implant of claim 1, wherein the first wall of the first member has a tubular configuration and the first wall of the second member has a tubular configuration, the first tubular wall of the first member and the first tubular wall of the second member being concentric with the longitudinal axis.

5. The orthopedic implant of claim 4, wherein the first wall of the third member has a tubular configuration, which is concentric with the longitudinal axis.

6. The orthopedic implant of claim 1, wherein the first wall of the third member further defines at least one lateral opening.

7. The orthopedic implant of claim 1, wherein the first wall of the third member further defines a transverse portion, which defines at least a portion of the chamber.

8. The orthopedic implant of claim 1, wherein the members each have a tubular configuration such that the first wall of the third member is configured for slidable disposal within the first wall of the second member, and the first wall of the second member is configured for slidable disposal within the first wall of the first member in the telescopic arrangement.

9. The orthopedic implant of claim 1, wherein in the first orientation the members are disposed in a nested configuration such that the second member and the third member are disposed within the first wall of the first member.

10. The orthopedic implant of claim 1, wherein the members are configured for expansion along the longitudinal axis only.

11. The orthopedic implant of claim 1, wherein the first wall of the first member includes an inner flange, the first wall of the second member includes an inner flange and an outer flange and the first wall of the third member includes an outer flange, such that in the second orientation the inner flange of the first member seals with the outer flange of the second member and the inner flange of the second member seals with the outer flange of the third member.

12. The orthopedic implant of claim 1, wherein the members each have a tubular configuration such that the first wall of the first member is configured for slidable disposal within the first wall of the second member and the first wall of the second member is configured for slidable disposal within the first wall of the third member in the telescopic arrangement.

13. The orthopedic implant of claim 1, further comprising a flexible layer disposed circumferentially about the first walls of the members to define the chamber.

14. The orthopedic implant of claim 13, wherein the flexible layer extends from a first end to a second end, the first end being connected to the first member and the second end being connected to the third member such that in the first orientation, the layer has a collapsed configuration and in the second orientation the layer is expanded along the longitudinal axis.

15. The orthopedic implant of claim 1, wherein the first walls of the members define an interior cavity disposed within a circumference of the chamber and separated from the chamber by the first walls of the members.

16. An orthopedic implant comprising:
a first member defining a longitudinal axis, a first wall and a second wall, the first wall defining at least a portion of a chamber and the second wall defining a first axial face comprising an opening defining a first graft containment cavity, the chamber being separate from the first graft containment cavity, wherein the first member defines a fluid receiving port configured to communicate with the chamber only, the first member includes a transverse wall separating the chamber and the first graft containment cavity, the transverse wall has a reservoir therein in communication with the chamber, and the implant comprises a lumen connecting the reservoir with the fluid receiving port;
a second member defining a first wall having an outer surface configured to engage an inner surface of the first wall of the first member such that the first wall of the second member is disposed for sealed engagement with the first wall of the first member, the first wall of the second member defining at least a portion of the chamber, the second member being configured for movement along the longitudinal axis relative to the first member; and
a third member defining a first wall having an outer surface configured to engage an inner surface of the first wall of the second member such that the first wall of the third member is disposed for sealed engagement with the first wall of the second member, the first wall of the third member defining at least a portion of the chamber and a second axial face opposite the first axial face comprising an opening defining a second graft containment cavity, the chamber being separate from the second graft containment cavity, the third member being configured for movement along the longitudinal axis relative to the second member; and
a flexible layer disposed circumferentially about the first wall of the members to define the chamber, the members and the flexible layer are expandable under a fluid pressure in the chamber for movement between a first orientation and a second orientation such that the first member and the third member are disposed to engage adjacent bone surfaces.

17. An orthopedic implant system comprising:
a first cylinder defining a longitudinal axis, a first tubular portion, a second tubular portion and a transverse wall therebetween, the first tubular portion defining at least a portion of a chamber and the second tubular portion including a plurality of openings and defining a first axial face comprising an opening defining a first graft containment cavity, the chamber being separate from the first graft containment cavity by the transverse wall, the first cylinder further defining a fluid receiving port configured to communicate with the chamber;
a second cylinder defining a first tubular portion having an outer surface configured to engage an inner surface of the first tubular portion of the first cylinder such that the first tubular portion of the second cylinder is disposed for sealed engagement with the first tubular portion of the first cylinder, the first tubular portion of the second cylinder defining at least a portion of the chamber, the second cylinder being configured for movement along the longitudinal axis relative to the first cylinder; and
a third cylinder defining a first tubular portion having an outer surface configured to engage an inner surface of the first tubular portion of the second cylinder such that the first tubular portion of the third cylinder is disposed for sealed engagement with the first tubular portion of the second cylinder, the first tubular portion of the third cylinder defining at least a portion of the chamber and including a plurality of openings and a second axial face opposite the first axial face, the second axial face comprising an opening defining a second graft containment cavity, the chamber being separate from the second graft containment cavity, the third cylinder being configured for movement along the longitudinal axis relative to the second cylinder; and bone graft configured for disposal in the first graft containment cavity and/or the second graft containment cavity, wherein the cylinders are concentric with the longitudinal axis and disposed in a telescopic arrangement such that the sealed engagement of the cylinders facilitates expansion of the cylinders under a fluid pressure in the chamber for movement between a first orientation such that the cylinders are disposed in a nested configuration and a second orientation such that the first cylinder and the third cylinder are disposed to engage adjacent bone surfaces.

* * * * *